United States Patent [19]
Kocsi

[11] Patent Number: 6,129,714
[45] Date of Patent: Oct. 10, 2000

[54] MEDICAL DRAINAGE MEANS

[76] Inventor: Louis Kocsi, 25 Palisade Ave., Garfield, N.J. 07026

[21] Appl. No.: 09/161,000

[22] Filed: Sep. 25, 1998

[51] Int. Cl.[7] ........................... A61M 35/00; F16K 15/00
[52] U.S. Cl. ........................ 604/323; 604/324; 137/511
[58] Field of Search ........................... 604/327, 332–335, 604/340–350, 323–326; 128/DIG. 24; 137/846, 847, 511, 513.3; 206/828

[56] References Cited

U.S. PATENT DOCUMENTS

| | | | |
|---|---|---|---|
| 3,661,143 | 5/1972 | Hankin | 128/DIG. 24 |
| 3,823,716 | 7/1974 | Hale | 128/DIG. 24 |
| 3,838,691 | 10/1974 | Paluden et al. | 604/323 |
| 3,901,272 | 8/1975 | Banners et al. | 137/513.5 |
| 4,085,755 | 4/1978 | Burrage | 128/DIG. 24 |
| 4,772,278 | 9/1988 | Baber | 604/324 |

*Primary Examiner*—John G. Weiss
*Assistant Examiner*—Carie Mager
*Attorney, Agent, or Firm*—MK Silverman

[57] ABSTRACT

An urinary drainage unit including a fluid-tight bag of a material, a major portion of which is flexible. The bag includes a liquid inlet and a gas outlet, both situated at a top of the bag which includes a liquid outlet at its bottom. The unit also includes a normally closed flutter valve (also known as a duckbill valve) having opposing lips, the valve extending integrally downwardly from the liquid inlet and disposed internally to the bag within its flexible portion, the flutter valve including a longitudinally disposed wire, between its lips, in which potential liquid flow across the liquid inlet, caused by an excess of internal bag pressure over body generated inlet pressure, is minimized by a venting function of the wire.

4 Claims, 3 Drawing Sheets

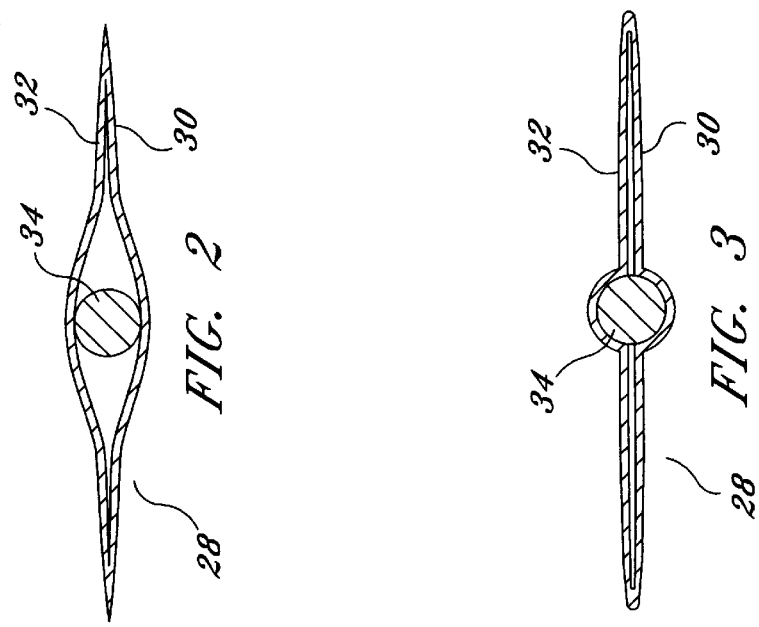
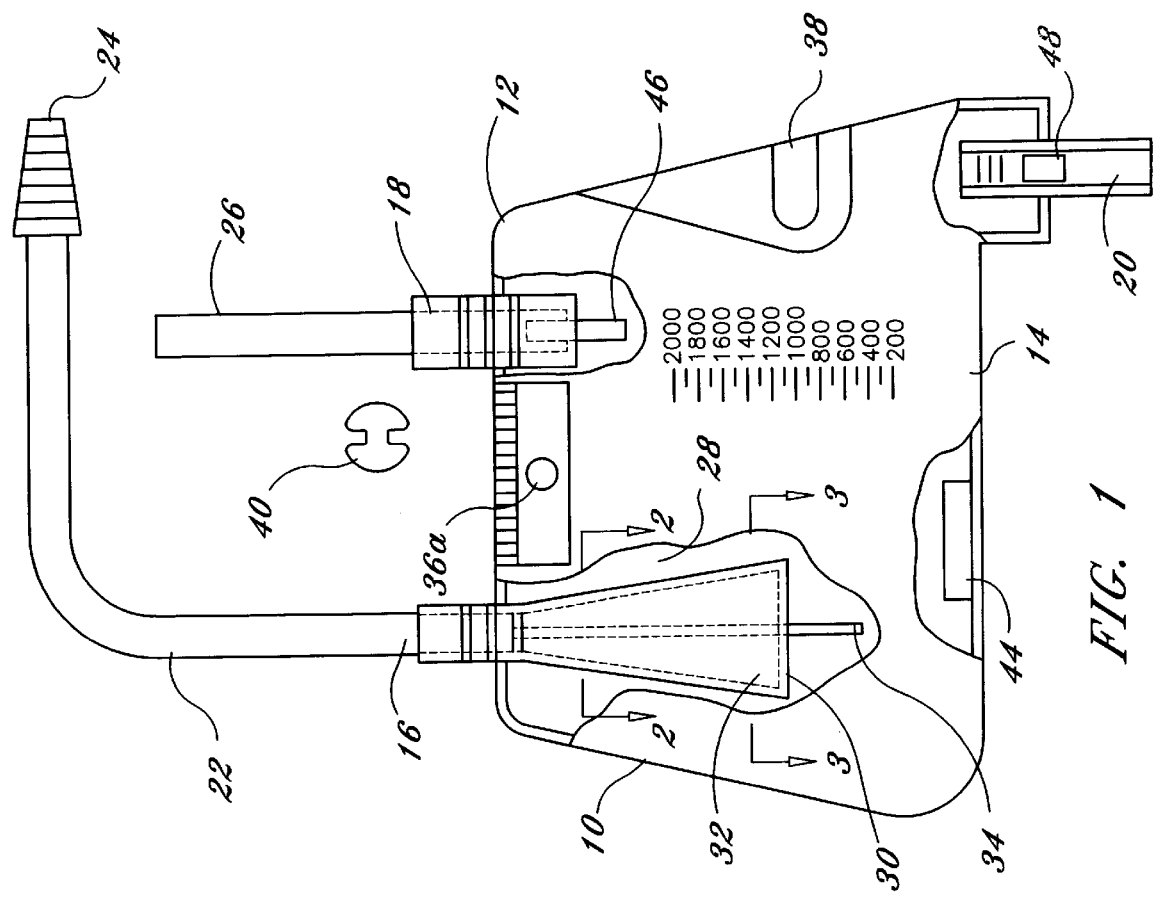

MEDICAL DRAINAGE MEANS

BACKGROUND OF THE INVENTION

The present invention relates to a medico-surgical drainage container and, more particularly, to an urinary drainage means of a type used by persons suffering from certain disease states and recovering from certain forms of surgery of the urethra.

The need for such urinary drainage means arises as a result of the natural build-up of urine in the bladder which occurs on a continuous basis, and cannot be stopped. Accordingly, periodic relief of such build-up of fluid in the bladder is a requirement of any patient, including those resting upon a bed, stretcher or those positioned within a wheelchair.

The prior art of medico-surgical drainage containers, as applicable to the instant invention, is to the best knowledge of the inventor represented by U.S. Pat. No. 4,772,278 (1988) to Baber, entitled Medico-Surgical Drainage Container. Other representative prior art is reflected in U.S. Pat. No. 3,583,401 (1969) to Vallinancourt, entitled Closed Drainage System with Double Lumin Tube; U.S. Pat. No. 4,524,805 (1985) to Hoffman, entitled Normally Closed Duckbill Valve and Method of Manufacture; and U.S. Pat. No. 4,828,554 (1989) to Griffin, entitled One Way Valve for Leg Urinals or the Like.

In the above prior art, said patents to Baber and Hoffman teach medico-surgical drainage containers utilizing a so-called duckbill valve. It is toward the improvement of such medico-surgical containers making use of duckbill valves that the instant invention is directed.

As is, particularly, recognized by Vallinancourt above, a major problem in the operation of a closed urinary drainage system is that the liquid column in the drainage bag will often become static, that is, the tube of the drainage system normally extends downwardly from the level of the patient's bladder to a receptacle some distance lower. The weight of the liquid column will often result in the development of a negative pressure in the bladder, not only emptying it, but also tending to draw the bladder wall against the end of the catheter and even partly into the lumen thereof, with serious adverse effects to the patient. The occurrence of this phenomenon often manifests itself when the bag or collection container of the system is visibly compressed by the ambient atmosphere. During such conditions, the liquid column may on occasion appear to be moving upward toward the patient.

Methods heretofore proposed to alleviate or eliminate this condition include venting the system at a suitable point in its upper portion and the use of abnormally large diameter tubes. As for the latter method, a tube of more than nine millimeters internal diameter will release its liquid column when vigorously shaken and it is believed the tubing larger than thirteen millimeters internal diameter will allow free flow of the liquid as air enters the outlet and bubbles-up through the descending liquid. However, most closed systems actually use tubing in the range of five to twelve millimeters internal diameter and the substitution of larger tubing is not considered practical or convenient.

The entry of air into the lower end of a small single tube is prevented by the surface tens-ion of the liquid column at that point and the fact that there is normally no place for air to enter at the upper end of the tube. A number of prior art systems, including those to Baber and Hoffman above, make use of a duckbill ending to the liquid input to the drainage container in the belief that the configuration thereof will permit appropriate venting within the bag portion to preclude the development of the above described negative pressure in the bladder. It has, however, been determined, over extended usages of such systems, that the desired venting does not always occur, this due to sticking between the respective surfaces of the duckbill valve. When such sticking surfaces of the duckbill valve occurs, the entire venting function thereof is defeated. While the above reference to Hoffman discusses a possible solution to the problem, the inventor herein has determined that through the provision of a wire-like element placed longitudinally within the duckbill valve, the desired venting function of the duckbill and, thereby, suitable operation of the entire system, can be achieved.

SUMMARY OF THE INVENTION

The present invention relates to an urinary drainage unit including a fluid-tight bag of a material, a major portion of which is flexible. Said bag includes a liquid inlet and a gas outlet, both situated at a top of the bag which, further, includes a liquid outlet at a bottom thereof. The inventive unit also includes a normally closed flutter valve (also known as a duckbill valve) having opposing lips, the valve depending integrally downwardly from said liquid inlet and disposed internally to said bag within the flexible portion thereof, said flutter valve including a longitudinally disposed wire, between said lips, in which potential liquid flow across said liquid inlet, caused by an excess of internal bag pressure over body-generated inlet pressure, is minimized by a venting function of said wire.

It is accordingly an object of the present invention to provide a flutter or duckbill valve construction particularly adapted for use within a drainage bag portion of a medico-surgical drainage system.

It is another object of the present invention to provide a valve for use within an urinary drainage system which will minimize development of negative pressure within the system.

It is a yet further object to provide an urinary drainage unit having a self-venting valve internal to the fluid collection container thereof.

The above and yet other objects and advantage of the present invention will become apparent from the hereinafter set forth Brief Description of the Drawings, Detailed Description of the Invention, and claims appended herewith.

BRIEF DESCRIPTION OF THE DRAWINGS

FIG. 1 is a front elevational view of the drainage unit.

FIG. 2 is a transverse cross-sectional view taken through Line 2—2 of FIG. 1.

FIG. 3 is a transverse cross-sectional view taken along Line 3—3 of FIG. 1.

DETAILED DESCRIPTION OF THE INVENTION

Figure 6:
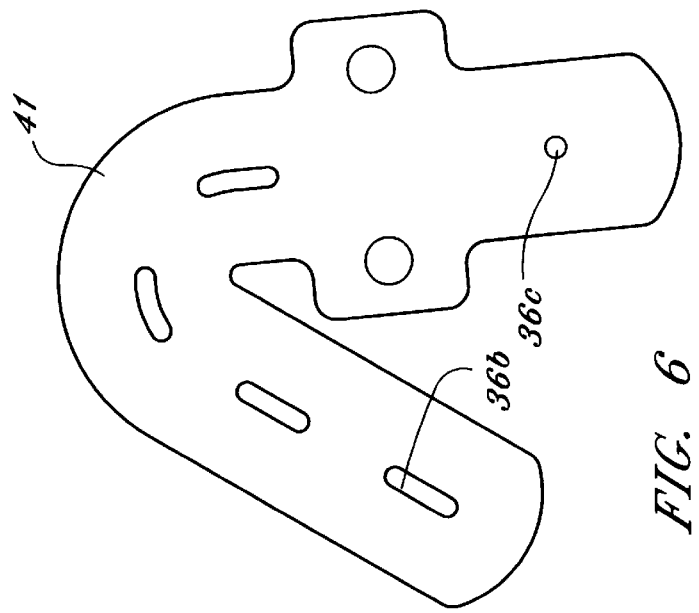
FIGS. 6 and 7 are perspective views of a drainage unit support strap and elements associated therewith.

With reference to the view of FIG. 1, the inventive medico-surgical drainage unit is seen to include a fluid-tight bag 10, typically formed of a polymeric material, a major portion of which must be of a flexible material in to accommodate the expansion thereof responsive to inflow and expansion of liquids and gases, as described below. Said bag 10 includes a top region 12 and a bottom region 14.

Within top region 12 is provided a liquid inlet 16 and gas outlet 18, while within bottom region 14 is provided a selectable liquid outlet 20. It is noted that said liquid inlet 16 comprises the lower end of a catheter 22 which, at an inlet 24 thereof, is inserted into the bladder of a patient. Connected to said gas outlet 18 is a tube 26, the function of which is to permit periodic release of gases within bag 10 that would otherwise build-up in a less than satisfactory fashion.

Figure 4:
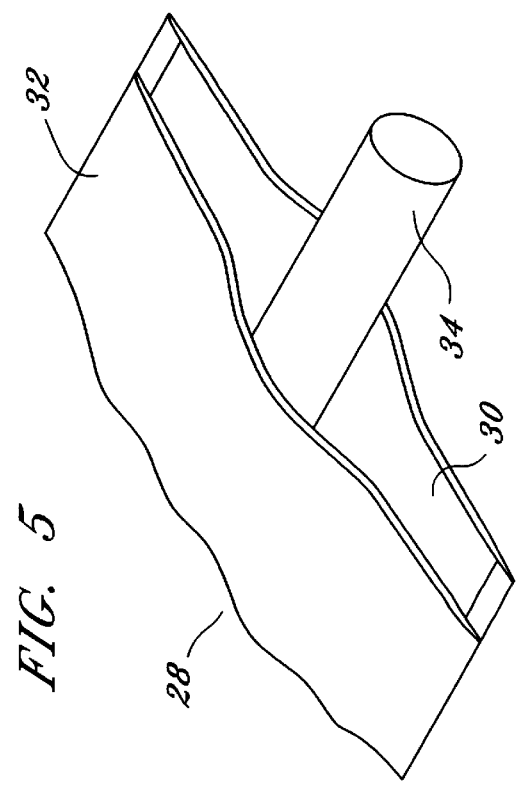
FIG. 4 is an enlarged perspective view of the mouth of the flutter valve.

Integrally depending from said liquid inlet 16 is a flutter valve 28 which, as may be noted as in the views of FIGS. 2 thru 4, includes opposing lips 30 and 32 and, further, includes a central longitudinally disposed wire 34, the purpose of which is to afford sufficient venting between lips 30 and 32 such that liquid within catheter 22 will not be subject to pressure from within bag 20 that would otherwise create so-called negative pressure across inlet 16 and catheter 22. It has been discovered that the normal function of flutter valve 28 (also known as a duckbill valve) is not impeded by the presence of wire 34 therewithin such that the flutter valve 28 can perform its basic function of assuring unidirectional flow of liquid in a downward direction through catheter 22, through fluid inlet 16 and through said flutter valve lips 30 and 32.

Also shown in the view of FIG. 1 are attachment areas of post 36 *a* and notch 38 by which the bag 10 may be secured to various means which are common in hospital and home-care environments. In connection therewith, there is further shown element 40 which facilitates attachment of area 36 to a catheter stand.

Figure 7:
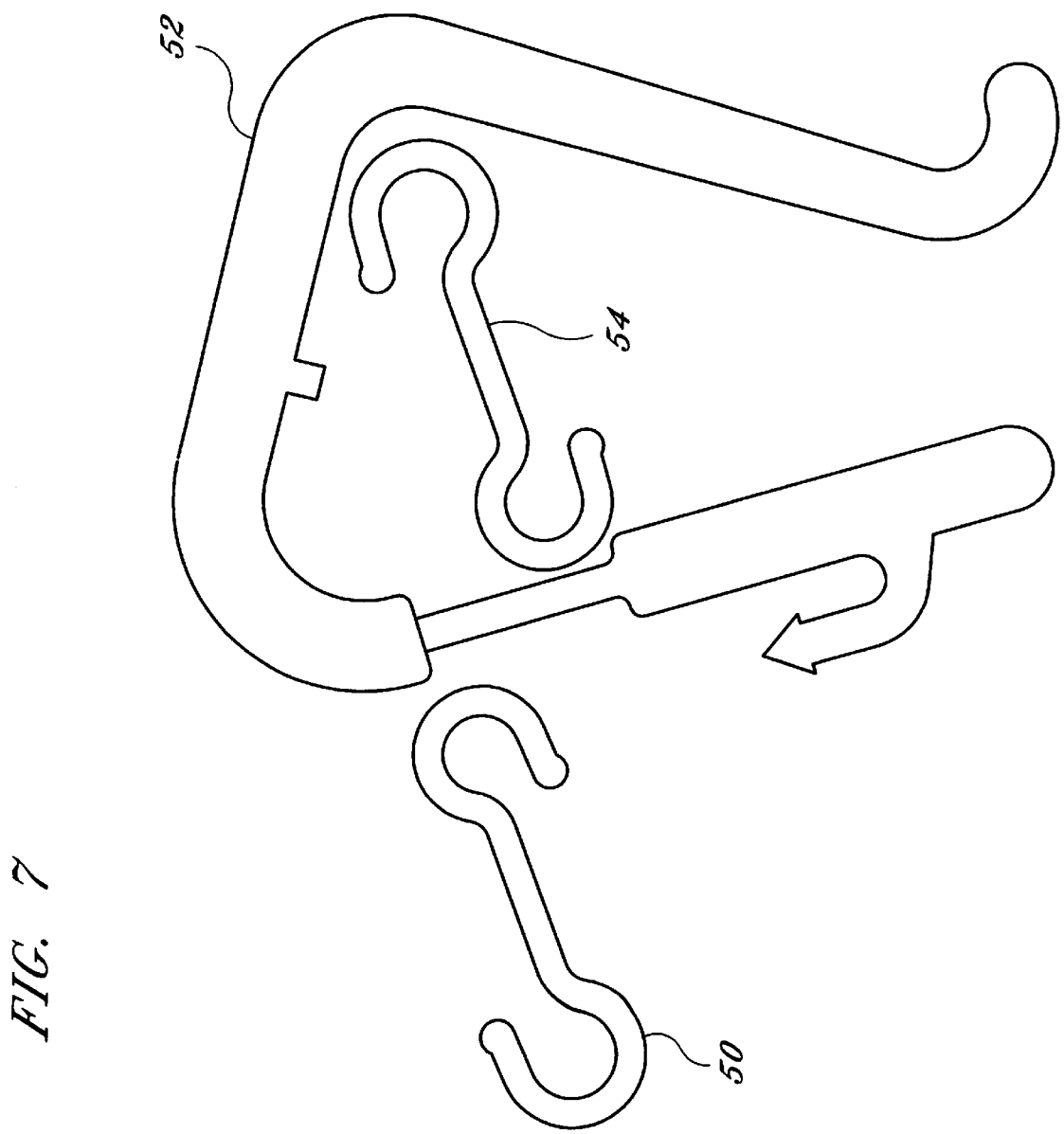

In FIGS. 6 and 7 are shown strap 41 including therein a slot 36*b* and hole 36*c* which, in combination with said post 36 (see FIG. 1) and said notch 38, taken with the unit suspension elements shown in FIG. 7, i.e., special purpose hooks 50, 52 and 54, facilitate the attachment of the bag 10 to a variety of environments such as a catheter stand and various home-care environments.

It is also noted that the inside of bag 10 may be provided with a porous internal chamber 44 within which may be provided a biodegradable odor neutralizer.

Such a neutralizer may, as desired, be placed within the fluid flow of gas outlet 18 or liquid outlet 20 as is indicated by elements 46 and 48 respectively. Use of such biodegradable deodorizing means in such outlets 18 and 20 will minimize the otherwise offensive odor typically associated with such bags. The functionality of such deodorant neutralizers in medico surgical bags is generally set forth in U.S. Pat. No. 4,367,742 (1983) to Ornstein, entitled Ostomy Bag.

Figure 5:
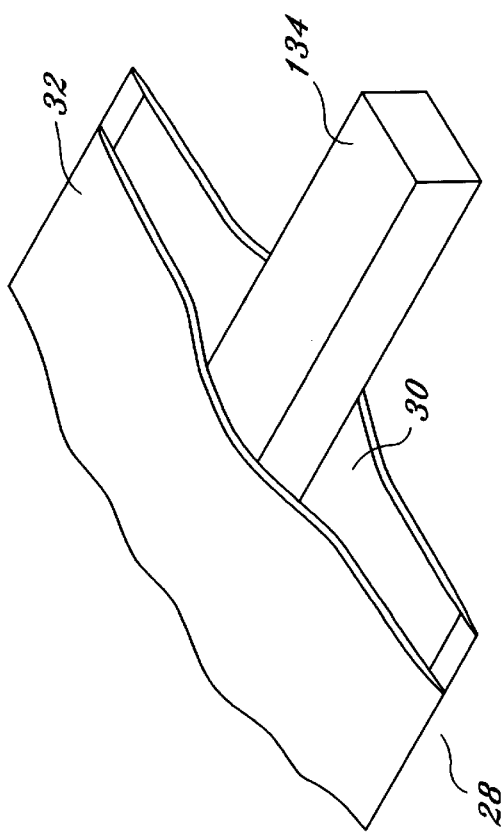
FIG. 5 is a perspective view of an alternative embodiment of the longitudinal wire of the flutter valve.

Shown in FIG. 5 is an alternate embodiment of the invention in which the longitudinally disposed wire 34 shown in FIGS. 1 thru 4 has been replaced by a wire 134 having a rectangular cross-section thereof. It has been found that a longitudinal wire having either a circular or rectangular cross-section will suitably function for purposes of the invention.

Accordingly, while there has been shown and described the preferred embodiment of the present invention it is to be appreciated that the invention may be embodied otherwise than is herein specifically shown and described and that, within said embodiments certain changes may be made in the form and arrangement of the parts without departing from the underlying idea or principles of this invention within the scope of the claims appended herewith.

Having thus described my invention what I claim as new, useful and non-obvious and, accordingly, secure by Letters Patent of the United States is:

1. A medico-surgical drainage unit comprising:
    (a) a fluid-tight bag of a material, a major portion of which is flexible, said bag having a top and a bottom, said bag having a liquid inlet and a gas outlet both situated at a top of said bag and, further, having a liquid outlet at a bottom thereof; and
    (b) a normally closed flutter valve having opposing lips, said flutter valve depending integrally from said liquid inlet, said flutter valve disposed internally to said bag within the flexible major portion thereof, said flutter valve including a longitudinally disposed wire between the opposing lips thereof, whereby potential back pressure of gas across said liquid inlet and into said catheter, caused by an excess of internal bag pressure, is minimized by a venting function of said flutter valve effected by said longitudinally disposed wire.

2. The medico-surgical drainage unit as recited in claim 1, further including a porous internal chamber within said fluid-tight bag containing, therein, a biodegradable odor neutralizing material.

3. The unit as recited in claim 2, in which said porous internal chamber is disposed within said gas outlet.

4. The unit as recited in claim 2, in which said internal chamber is disposed within said liquid outlet.

* * * * *